United States Patent [19]
Dellaporta et al.

[11] Patent Number: 6,011,200
[45] Date of Patent: Jan. 4, 2000

[54] METHODS FOR ALTERING THE RATE OF PLANT DEVELOPMENT AND PLANTS OBTAINED THEREFROM

[75] Inventors: Stephen L. Dellaporta, Branford, Conn.; Jychian Chen, Taipei, Taiwan

[73] Assignee: Yale University, New Haven, Conn.

[21] Appl. No.: 08/902,902

[22] Filed: Jul. 30, 1997

Related U.S. Application Data

[60] Provisional application No. 60/023,314, Jul. 31, 1996.

[51] Int. Cl.$^7$ ............................. C12N 5/04; C12N 15/29; C12N 15/62; A01H 5/00
[52] U.S. Cl. .......................... 800/285; 435/468; 435/410; 435/419; 536/23.6; 800/278; 800/286; 800/290; 800/295; 800/298; 800/306
[58] Field of Search .......................... 536/23.6; 800/278, 800/285, 306, 286, 290, 295, 298; 435/468, 410, 419

[56] References Cited

FOREIGN PATENT DOCUMENTS

WO 9614414  5/1996  WIPO .

OTHER PUBLICATIONS

Finnegan, E.J.: "The Role of DNA Methylation in Plant Development" *Epigenetic Mechanisms of Gene Regulation*, vol. 32, Dec. 6, 1996, Cold Spring Harbour Laboratory Press, pp. 127–140.

Kakutani, T., et al.: "Characterization of an Arabidopsis Thaliana DNA Hypomethylation Mutant" *Nucleic Acid Research*, vol. 23, No. 1, pp. 130–137.

Vongs, A. et al.: "Arabidopsis Thaliana DNA Methylation Mutants" *Science*, vol. 260, Jul. 25, 1993.

Finnegan, E.J. et al.: "Isolation and Identification by Sequence Homology of a Putative Cytosine Methyltransferase from Arabidopsis Thaliana" *Nucleic Acid Research*, vol. 21, No. 10, 1993, pp. 2383–2388.

Ronemus, M.J. et al.: "Demethylation–Induced Developmental Pleiotropy in Arabidopsis" *Science*, vol. 273, Aug. 2, 1996, pp. 654–657.

Finnegan, E.J. et al.: "Reduced DNA Methylation in Arabidopsis Thaliana Results in Abnormal Plant Development" *Proceedings of the National Academy of Sciences of the USA*, vol. 93, Aug. 1996, pp. 8449–8454.

Richards, E.J., et al.: "DNA Methylation and Plant Development" *Trends in Genetics*, vol. 13, No. 8, Aug. 1997, pp. 319–323.

Mitra et al. Biochim Biophys Acta. 1994. vol. 1219: 244–249.

Napoli et al. The Plant Cell. 1989. vol. 2: 278–289.

Smith et al. Nature. 1988. vol. 334: 724–726.

Khvoika et al. Biokhimiia. 1978. vol. 43: 996–1000.

Dwivedi et al. Plant Molecular Biology. 1994. vol. 26: 61–71.

Finnegan et al. Nucleic Acid Research. 1993. vol. 21: 2383–2388.

*Primary Examiner*—Lynette R. F. Smith
*Assistant Examiner*—Ousama Zaghmout
*Attorney, Agent, or Firm*—Morgan, Lewis & Bockius LLP

[57] ABSTRACT

The present invention is based on the unexpected observation that DNA methylation, particularly at cytosine residues, regulates the rate of development of a plant. Based on this observation, the present invention provides methods of increasing or decreasing the rate of development of a plant by either increasing or decreasing the amount of methylated DNA found in the plant. The present invention further provides plants that have been altered such that their rate of maturation is either increased or decreased relative to the rate of maturation of a non-altered plant.

21 Claims, 4 Drawing Sheets

METHODS FOR ALTERING THE RATE OF PLANT DEVELOPMENT AND PLANTS OBTAINED THEREFROM

This application claims the benefit of U.S. Provisional Application No. 60/023,314, filed Jul. 31, 1996, the specification of which is hereby incorporated by reference in its entirety.

STATEMENT OF RIGHTS TO INVENTIONS MADE UNDER FEDERALLY SPONSORED RESEARCH

This invention was made with governmental support under National Institutes of Health grant GM38148 and National Science Council grant 81-0203-B001-14. The Government has certain rights in the invention.

TECHNICAL FIELD

The present application is in the field of plant developmental biology and relates to methods for altering the rate at which a plant develops using molecular genetic techniques.

BACKGROUND ART

Plant genomes contain relatively large amounts of the modified nucleotide 5-methylcytosine ($5^m$C) (Y. Greenbaum, et al., Nature 292: 850 (1981)). Despite evidence implicating cytosine methylation in plant epigenetic phenomena, such as repeat-induced gene silencing (TIGS), cosuppression, and inactivation of transposable elements (F. F. Assaad, et al., Plant Mol. Biol. 22: 1,057 (1993); C. Napoli, et al., Plant Cell 2: 279 (1990); J. Bender et al., Cell 83: 725 (1995); P. S. Chomet, et al., Genetics 138: 213 (1994); R. A. Martienssen, et al., Curr. Opin. Genet. Dev. 5: 234 (1995); M. A. Matzke, et al., Plant Physiol., 107: 679–685 (1995)), the role of cytosine methylation in plant developmental processes is not clear.

In Arabidopsis, ddm mutants (decrease in DNA methylation) have been isolated with reduced levels of cytosine methylation in repetitive DNA sequences, although these mutations do not result in any detectable change in DNA methyltransferase enzymatic activity (A. Vongs, et al., Science, 260: 1,926 (1993), T. Kakutani, et al., Nucleic Acids Res. 23: 130 (1995)). After several generations of self-pollination, ddm mutants exhibit a slight delay (1.7 days) in flowering, altered leaf shape, and an increase in cauline leaf number (T. Kakutani, et al. (1995)).

The exact mechanisms that mediate plant development are presently not well understood. Plants that have an increased rate of development would be highly useful in plant breeding programs. Specifically, numerous plants, such as tree species, have extremely long generation times and therefore the number of crosses that can be generated within a given year or plant cycle is limited. In one extreme case, certain species of bamboo flower only once every one hundred years. Methods which could be used to decrease the maturation time would be highly beneficial in breeding programs involving many plants.

A reduction in the rate a plant matures can be used to increase the biomass production of a given plant. For numerous plants, increases in biomass yields would increase the economic value of the commercial plant. For example, flax, tobacco, alfalfa, spinach, lettuce, etc.

It is therefore the focus of the present invention to provide methods for increasing or decreasing the time required for a plant to mature as well as plants which are produced by these methods.

All references disclosed throughout this application are hereby incorporated by reference in their entirety.

DISCLOSURE OF THE INVENTION

The present invention is based on the unexpected observation that a decrease of about 70% in the amount of methylated DNA present in a plant genome results in a plant that requires more time to mature while an increase in the amount of methylated DNA present in a plant genome results in a plant that requires less time to mature. Based on these observations the present invention provides methods of altering a plant, plant cells, plant tissues or plant seeds, so as to obtain a plant that has an altered rate of maturation. In one method, the rate of maturation is increased by altering the plant, plant cells, plant tissues or plant seeds, using molecular techniques, such that the plant has a sufficient increase in methylated DNA so as to yield a plant that matures faster than a non-altered plant. In another embodiment, the rate of maturation is decreased by altering a plant, plant cells, plant tissues or plant seeds, using molecular techniques, such that the plant has a sufficient decrease in methylated DNA so as to yield a plant that matures slower than a non-altered plant.

The present invention further provides plants that have an altered rate of maturation that have been produced using the methods herein described.

GENERAL DESCRIPTION

BEST MODE FOR CARRYING OUT THE INVENTION

General Description

Figure 1:
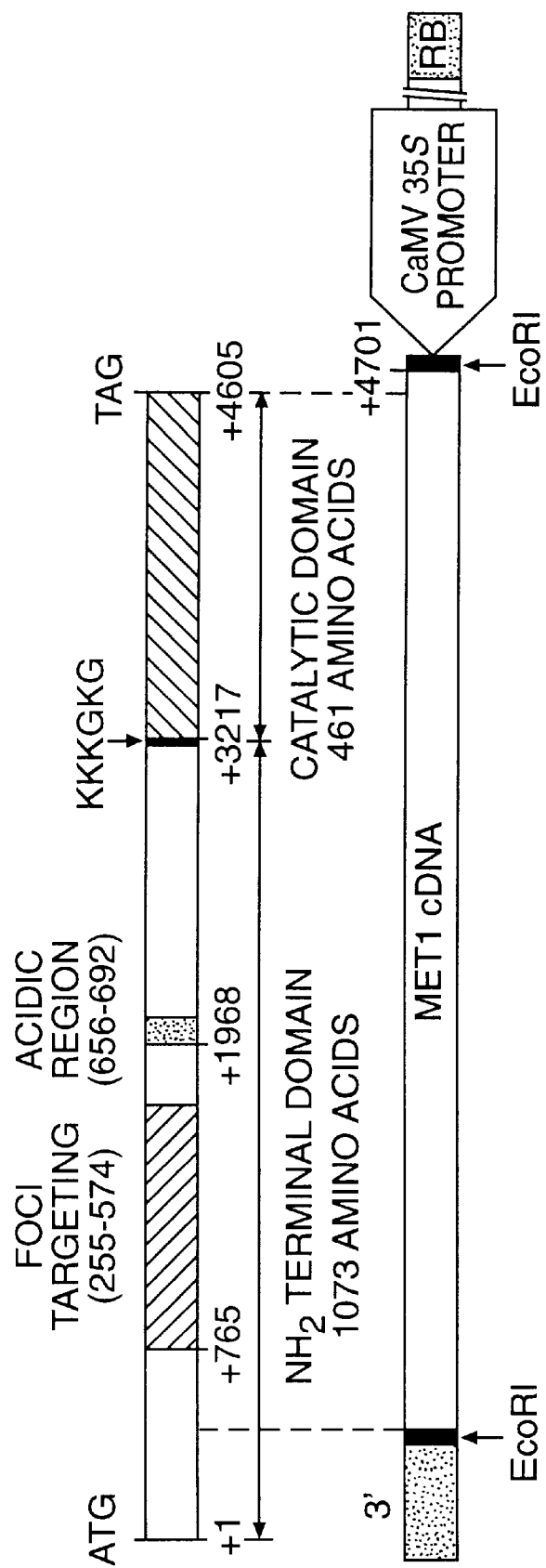
FIG. 1. The predicted MET1 gene product and antisense construct. A diagrammatic representation of the predicted gene product of the MET1 locus is provided. The MET1 protein is a 1,534-amino acid protein with a high degree of homology to the mouse MTase, particularly in the catalytic and $NH_2$-terminal foci targeting domains (E. J. Finnegan, et al., Nucleic Acids Res. 21: 2,383 (1993)). The MET1 antisense construct is shown in the bottom of the figure. See Example 1.

The present invention is based on the unexpected observation that DNA methylation, particularly at cytosine nucleotides, is involved in regulating the rate of plant development and maturation, particularly the rate at which flower producing organs and structures mature. Specifically, the present invention is based on the observation that decreasing the amount of methylated DNA results in plants that mature at a slower rate than plants containing normal amounts of methylated DNA while increasing the amount of methylated DNA leads to plants that mature at a faster rate than plants with normal amounts of methylated DNA.

Based on these observations, the present invention provides methods for altering the rate of maturation of a plant which comprises the step of genetically altering the plant, using molecular techniques, so the plant has an altered degree of DNA methylation when compared to a non-altered plant sufficient to alter the rate at which the plant develops.

As used herein, maturation refers to the process of plant differentiation leading to the production of flowers and other reproductive tissues. The rate of maturation is said to be altered when the rate at which the plant develops flowers is either increased or decreased relative to a non-altered plant. The degree that the rate of maturation is altered will vary from plant to plant as well as between plants that have been altered using different methods.

In a preferred embodiment, the method will produce plants with an increased rate of maturation of about 10% to about 25% faster, more preferably about 25% to about 50% faster, than the normal rate of maturation. For example, in Arabidopsis, flowers typically develop after 26 days under long day conditions. In the Examples, Arabidopsis plants were obtained which developed flowers after 10 to 12 days.

The result of accelerating plant development is the ability to decrease the generational time in plant breeding programs. Plants that have been altered using the methods herein described for decreasing maturation times can be used in any conventional breeding program, producing accelerated results.

In another preferred embodiment, the methods of the present invention will produce plants with a decreased rate of maturation that is about 10% to about 25% slower, more preferably about 25% to about 50% slower, most preferably about 50% to about 100% or more slower than the normal rate of maturation. In the Examples, altered Arabidopsis plants were obtained that matured and produced flowers at 45–47 days, representing an almost 100% increase in the days required for maturation when compared to non-altered plants.

When used to slow the rate of maturation, the present methods produce plants that have increased biomass. As used herein, biomass refers to the total plant weight, particularly leafy material. The amount of leaf material is increased in plants altered to have a slower rate of maturation.

Another consequence of delaying flower production is to produce plants that have more secondary branches and axial nodes. As a result, the plant, when it matures, produces a larger number of flower organs than does the non-altered plant.

Any plant that can be genetically altered using molecular techniques and any plants propagated containing the genetic alteration can be used in the present method. Methods known in the art for molecularly altering a plant are discussed in detail below. The preferred plants include both dicot and monocotyledonous plants. The most preferred plants are plants with economic value as a food or biomass source, or plants with long maturation times. Such plants include, but are not limited to, leafy plants such as tobacco, spinach, lettuce, and seed bearing plants such as rice, corn, soy bean etc.

The methods of the present invention rely on altering plants using molecular techniques. As used herein, molecular techniques exclude classical genetic techniques such as breeding/selection, identification of random mutagenesis and chemical mutagenesis techniques. Molecular techniques refers to procedures in which DNA is manipulated in a test tube during at least one stage of the process, such as the direct manipulation of DNA or the use of shuttle host such as bacterium. Such methods are well known in the art and are described in, for example, Sambrook, et al., *Molecular Cloning: a Laboratory Manual,* Cold Spring Harbor Press (1989). Some of the techniques that are used to alter a plant are discussed in more detail below. Molecular techniques are differentiated from classical genetics in which randomly occurring spontaneous mutants or classical mutagenic techniques are applied to a given plant type.

The requirement of the use of molecular techniques is to avoid the present invention reading on altered plants presently known in the art that have been generated through non-molecular techniques such as random mutation. Such plants may be known to have an altered rate of development but the underlying mechanism was not known prior to the present invention. Based on the present invention, it is likely that such plants will be found to have alterations in DNA methylation.

Although the present invention is based on the use of molecular techniques, a skilled artisan can now employ a new selection criteria when altering plants using non-molecular methods; namely selecting plants generated through methods such as chemical mutagenesis for increased or decreased DNA methylation. Specifically, plants and plant cells can be subjected to chemical mutagenesis, physical mutagenesis and the like and the resulting plant selected based on alterations in amount of DNA methylation or in the activity of the DNA methyl transferase. Plants can then be further propagated from the isolated and identified variants as having altered amounts of DNA that then correlates to an altered rate of maturation.

Methods to Decrease the Rate of Maturation

As provided above, the methods of the present invention can be used to alter plants such that the rate of maturation is decreased, thus producing plants that require more time to mature. To obtain a plant that has a reduced rate of maturation when compared to a non-altered plant, molecular techniques are used to reduce the amount of methylated DNA present in the altered plant.

As used herein, a plant is said to have a reduced or decreased amount of methylated DNA when the plant has less methylated DNA than the non-altered plant. Of the four nucleotides, cytosine has been seen to be methylated in plants. The present methods are therefore accomplished by targeting the methylation of cytosine.

What is contemplated is a reduction sufficient and effective to alter the rate of maturation in a manner useful for the purposes outlined herein. Thus any alteration in the amount of DNA methylation, so long as it results in an altered rate of development, is contemplated by the present invention.

In the preferred embodiment, the method of the present invention will result in plants having about a 10% to about a 25% reduction, more preferable about a 25% to about a 50% reduction, most preferably about a 50% to about a 70% or greater reduction in the amount of methylated DNA present when compared to non-altered plants. In the Examples that follows, plants having a 75% reduction in methylated cytosine were obtained.

A variety of targets, strategies and molecular techniques can be used by a skilled artisan to reduce the amount of methylated DNA present in a plant. For example, to obtain a reduction in the amount of methylated DNA, molecular techniques can be used to reduce the level of expression or inactivate the gene encoding one or more DNA methyl transferases that are normally produced in the plant. The methyl transferase can be altered in a variety of ways by a skilled artisan so as to obtain a reduction in the amount of methylated DNA in the plant.

Any of a plant's DNA methyl transferases genes can be used as a target in the present method. The most preferred targets are the genes encoding a cytosine methyl transferase. Examples of DNA methyl transferase genes known in the art include cytosine methyltransferase, such as the MET1 Arabidopsis gene herein used, the human and mouse analogs, and microbial methyl transferases such as bacterial GC methyl transferase (for example, see Finnegan et al., (1995)).

In the examples that follow, an antisense DNA expression element was created in which a fragment of a plant DNA methyl transferase gene was placed into an expression vector and inserted to a plant such that an mRNA was produced that is complimentary to mRNA encoding a plant DNA methyl transferase. A skilled artisan can readily follow this procedure with any DNA methyl transferase gene, or fragment thereof Further, a skilled artisan can readily obtain a DNA methyl transferase gene from any desired plant for use in the present methods. The preparation of antisense expression vectors is discussed in detail below.

An alternative strategy to decrease the amount of methylated DNA present in a plant is to create knockout mutants in the plant in which one or more of the plant's DNA methyl transferase genes are inactivated. This can be accomplished through the use of homologous recombination to insert stop codons or large DNA fragments within the coding region of a plant DNA methyl transferase gene. Alternatively, transposon mediated mutagenesis can be used for the same purpose. The preparation of recombination vectors is discussed in detail below.

Plants that have been altered to contain a reduced amount of methylated DNA can be further altered so as to contain an expression unit that expresses a DNA methyl transferase that is expressed or is functional under inducible conditions. Such plants are of additional value because of the ability to induce expression of a DNA methyl transferase gene, allowing one to activate or deactivate methyl transferase expression thus creating the ability to control alterations in the rate of maturation. The preparation of inducible expression vectors is discussed in detail below.

Methods to Increase the Rate of Maturation

As provided above, the methods of the present invention can be used to alter plants such that the rate of maturation is increased, thus producing plants that require less time to mature. To obtain a plant that has an increased rate of maturation when compared to a non-altered plant, molecular techniques are used to increase the amount of methylated DNA present in the altered plant.

As used herein, a plant is said to have a reduced or decreased amount of methylated DNA when the plant has less methylated DNA than the non-altered plant. Of the four nucleotides, cytosine has been seen to be methylated in plants. The present methods are therefore accomplished by targeting the methylation of cytosine.

In the preferred embodiment, the method of the present invention will result in plants having about a 10% to about a 25% increase, more preferable about a 25% to about a 50% increase, most preferably about a 50% to about a 70% or greater increase in the amount of methylated DNA present when compared to non-altered plants. In the Examples that follows, plants having an increase in methylated cytosine were obtained.

A variety of targets, strategies and molecular techniques can be used by a skilled artisan to increase the amount of methylated DNA present in the plant. For example, to obtain an increase in the amount of methylated DNA, molecular techniques can be used to increase the level of one or more DNA methyl transferases in the plant cell. The methyl transferase can be altered in a variety of ways by a skilled artisan so as to obtain an increase in the amount of methylated DNA in the plant.

For example, DNA methyl transferase encoding expression units can be inserted into a plant genome using molecular techniques. Such methyl transferase expression units can be controlled either by a constitutive promoter, providing continuous expression of the DNA methyl transferase gene, or using an inducible promoter, allowing one to turn on or off the expression of DNA methyl transferase. By controlling the level at which the DNA methyl transferase is expressed, through the use of specific promoter sequences or by altering a plant to contain one or more additional copies of a DNA methyl transferase gene, the amount of methylated DNA found in the plant can be dramatically increased.

Any DNA methyl transferase gene, or active fragment thereof, can be used to alter a plant such that the plant will contain an increased amount of methylated DNA, so long as the DNA methyl transferase gene can be modified so that it is expressed in a plant. In the examples that follow, the MET1 DNA methyl transferase gene from Arabidopsis was utilized. This gene, or its homologue from another plant, can readily be used by a skilled artisan in any plant system. The construction of expression units encoding a DNA methyl transferase is described in detail below.

Plants that have been altered to contain a increased amount of methylated DNA can be further altered so as to contain an expression unit that expresses a DNA methyl transferase that is expressed or is functional under inducible conditions. Such plants are of additional value because of the ability to induce expression of a DNA methyl transferase gene, allowing one to activate or deactivate methyl transferase expression thus creating the ability to control alterations in the rate of maturation. The preparation of inducible expression vectors is discussed in detail below.

Plants with Altered Maturation Rates.

The present invention further provides plants that have been altered using molecular techniques so that they have an altered rate of maturation. As provided above, such plants will mature at a rate that is either slower than, or faster than, non-altered plants, depending on whether the amount of methylated DNA present is either increased or decreased relative to the amount present in a non-altered plant cell respectively. The plants of the present invention fall within two types. The first type are plants that have an increased rate of maturation while the second type are plants that have a reduced rate of maturation.

The preferred plants of the present invention that have an increased rate of maturation, will mature at a rate which is about 10% to about 25% faster, more preferably about 25% to about 50% faster, than the non-altered plant. The preferred plants of the present invention that have a slower rate of maturation will mature at a rate which is about 10% to about 25% slower, more preferably about 25% to about 50% slower, most preferably about 50% to about 100% slower than a non-altered plant.

The plants or the present invention include those that have been altered, using molecular techniques, to have an altered amount of methylated DNA sufficient to alter the rate of maturation of the plant. The plants of the present invention therefore include any plant that can be altered using molecular technique so as to alter the amount of methylated DNA present in the plant. The preferred plants are plants for which it is desirable to reduce generation times for breeding or seed production purposes or plants that are used for biomass production. Particularly useful plants include, but are not limited to, corn, rice, soy bean, wheat, spinach, lettuce, alfalfa, etc.

Expression Units to Express Exogenous DNA in a Plant

As provided above, several embodiments of the present invention employ expression units (or expression vectors or systems) to express an exogenously supplied gene, such as a DNA methyl transferase, or antisense molecule, in a plant. Methods for generating expression units/systems/vectors for use in plants are well known in the art and can readily be adapted for use in altering the amount of methylated DNA present in a plant cell. Typically, such units employ a protein or antisense coding region, such as the MET1 Arabidopsis gene, or a homologue thereof, and one or more expression control elements. The choice of the protein/antisense coding region, as well as the control elements, employed will be based on the effect desired (i.e., reduction or increase in the amount of DNA methylation), the plant that is to be altered, the method chosen for altering the amount of methylated DNA and the transformation system used. A skilled artisan can readily use any appropriate plant/vector/expression system in the present methods following the outline provided herein.

The expression control elements used to regulate the expression of the protein or antisense coding region can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumafacians*. Alternatively, plant viral promoters can also be used, such as the cauliflower mosaic virus 35S promoter to control gene expression in a plant. Lastly, plant promoters such as prolifera promoter, fruit-specific promoters, Ap3 promoter, heat shock promoters, seed-specific promoters, etc. can also be used. The most preferred promoters will be active in dividing tissue, particularly meristematic cells.

Either a constitutive promoter (such as the CaMV or Nos promoter illustrated above), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein or antisense coding sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the Agrobacterium octopine synthase signal (Gielen et al., *EMBO J* 3: 835–846 (1984)) or the nopaline synthase signal (Depicker et al., *Mol. and Appl. Genet.* 1: 561–573 (1982)).

The resulting expression unit is ligated into or otherwise constructed to be included in a vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

Methods to produce antisense encoding vectors

As discussed above, plants having an altered amount of methylated DNA can be produced by using antisense sequences for interrupting the expression of one or more DNA methyl transferases in a plant cell. As evidenced by the behavior of antisense mutants described in the Examples, reduction in DNA methylation results in plants with reduced maturation rates while increases in DNA methylation results in plants with increased maturation rates. Accordingly, antisense sequences of suitable length can be transfected into plant cells, using the methods described herein, to obtain plants that take longer or shorter to mature than the non-altered plant. Methods for inhibiting expression in plants using antisense constructs, including generation of antisense sequences in situ are described, for example, in U.S. Pat. Nos. 5,107,065 and 5,254,800.

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See H. E. Moser, et al., *Science* 238: 645–650 (1987) and M. Cooney, et al., *Science* 241: 456–459 (1988)). Regions in the control sequences containing stretches of purine bases are particularly attractive targets. Triple helix formation along with photocrosslinking is described, e.g., in D. Praseuth, et al., *Proc. Nat'l Acad. Sci. USA* 85: 1,349–1,353 (1988).

Inactivation of Endogenous Methyl transferases or transferases

Another approach to inactivate one or more endogenous DNA plant genes that encode a DNA methyl transferase employs homologous recombination to disrupt the gene. The techniques for recombinational inactivation are known in the art and can readily be adapted to the present invention, for example see D. K. Asch, et al., *Mol. Gen. Genet.* 221: 37–43 (1990); K. K. Asch, et al., *Genetics* 130: 737–748 (1992).

Transformation of Plant Cells

When an appropriate vector is obtained, for example as described above, transgenic plants are prepared which contain the desired expression unit or into which a recombination inactivation vector has been introduced. In one method of transformation, the vector is microinjected directly into plant cells by use of micropipettes to mechanically transfer the recombinant DNA into the plant cell (Crossway, *Mol. Gen. Genetics* 202: 179–185 (1985)). In another method, the genetic material is transferred into the plant cell using polyethylene glycol (Krens, et al., *Nature* 296: 72–74 (1982)), or high velocity ballistic penetration by small particles with the nucleic acid either within the matrix of small beads or particles, or on the surface, is used (Klein, et al., *Nature* 327: 70–73 (1987)). In still another method protoplasts are fused with other entities which contain the DNA whose introduction is desired. These entities are minicells, cells, lysosomes or other fusible lipid-surfaced bodies (Fraley, et al., *Proc. Nat'l Acad. Sci. USA* 79: 1,859–1,863 (1982)).

DNA may also be introduced into the plant cells by electroporation (From et al., *Proc. Nat'l Acad. Sci. USA* 82: 5,824 (1985)). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (J. Schell, *Science* 237: 1,176–1,183 (1987)). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* 303: 179–189 (1983)). The transferred DNA region can be increased in size by the insertion-of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and RI plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel, *Nature* 298: 85–88 (1981)), promoters (Lawton et al., *Plant Mol. Biol.* 9: 315–324 (1987)) and structural genes for antibiotic resistance as a selection factor (Fraley et al., *Proc. Nat'l Acad Sci.* 80: 4,803–4,807 (1983)).

There are two classes of recombinant Ti and Ri plasmid vector systems now in use. In one class, called "co-integrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* 3: 1,681–1,689 (1984) and the non-oncogenic Ti plasmid pGV3850, described by Zambryski et al., *EMBO J* 2: 2,143–2,150(1983). In the second class or "binary" system, the gene of interest is inserted into a shuttle vector containing the cis-acting elements required for plant transformation. The other necessary functions are provided in trans by the non-oncogenic Ti plasmid, as exemplified by the pBIN19 shuttle vector described by Bevan, *Nucleic Acids Res.* 12: 8,711–8,721 (1984) and the non-oncogenic Ti plasmid pAL4404 described by Hoekma, et al., (1983). Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al., *Nature* 311: 763–764 (1984)). However, there is growing evidence now that certain monocots can be transformed by Agrobacterium. Using novel experimental approaches cereal species such as rye (de la Pena et al., Nature 325: 274–276 (1987)), maize (Rhodes et al., *Science* 240: 204–207 (1988)), and rice (Shimamoto et al., *Nature* 338: 274–276 (1989)) may now be transformed.

Identification of transformed cells or plants is generally accomplished by including a selectable marker in the transforming vector, or by obtaining evidence of successful bacterial infection.

Regeneration of Transformed Plants

Plant cells which have been transformed can also be regenerated using known techniques. For example, plant regeneration from cultured protoplasts is described in Evans et al., *Handbook of Plant Cell Cultures*, Vol. I: (MacMillan Publishing Co. New York, 1983); and I. R. Vasil (ed.), *Cell Culture and Somatic Cell Genetics of Plants*, (Acad. Press, Orlando, Vol. 1, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Silencing of Transgenes

It has been observed that many exogenously supplied expression units that are introduced into a plant are not expressed at the level that might be expected based on the promoter and control sequences employed (M. Matzke, et al., (1995)). The inactivation of transgenes is known as silencing. Using the plants of the present invention, it has been observed that many introduced expression units become inactivated as a result of DNA methylation. Accordingly, the methods used to alter the amount of DNA methylation present in a plant, and plants generated through such methods, can be further used to control the level of expression of an introduced expression unit.

The following examples are provided to illustrate, but not limit, the present invention. All references herein referred to are hereby incorporated by reference.

EXAMPLE 1

Plants with Reduced Rates of Maturation

1. Construction of antisense expression vectors

A 4.3 kb MET1 cDNA spanning the positions indicated in FIG. 1 was inserted in the reverse orientation with respect to the CaMV 35S promoter in the pMON530 T-DNA vector. MET1 cDNA B5-2 was cloned into the Eco RI site of T-DNA vector pMON530 (Monsanto) in the antisense orientation to the CaMV 35S promoter through use of Eco RI sites present in cDNA linkers. The pMON530 T-DNA confers resistance to kanamycin (50 μg/mi) on transgenic plants.

2. Southern analysis of repetitive and single-copy DNA methylation patterns.

Total genomic DNA (3 μg/lane) from antisense lines, wild type, and the ddm1 mutant were digested with Hpa II (FIG. 2 left panels) or Msp I (FIG. 2 right panels), subjected to electrophoresis in 0.8% agarose, and transferred to Zeta-Probe membranes (Bio-Rad) and hybridized as described to various probes (J. Chen, et al., in *The Maize Handbook*, M. Freeling, et al., (Springer-Verlag, New York, 1994), pp. 525–527 and S. L. Dellaporta, et al., ibid, pp. 559–572). The filters were probed with a 180-bp centromere repeat (J. M. Martinez-Zapater, et al., (1985)) and 55 rDNA (B. R. Campbell, et al., (1992)) (Upper panels), or were probed with four single-copy gene probes—PHOSPHORIBOSYLANTHRANLATE TRANSFERASE 1 (PAT1), PROLIFERA (PRL), CONSTITUTIVELY PHOTOMORPHOGENIC 1 (COP1), and ERECTA (ER) (Lower panels).

3. Southern and phenotypic analyses of Tr246 outcross progeny

Figure 3:
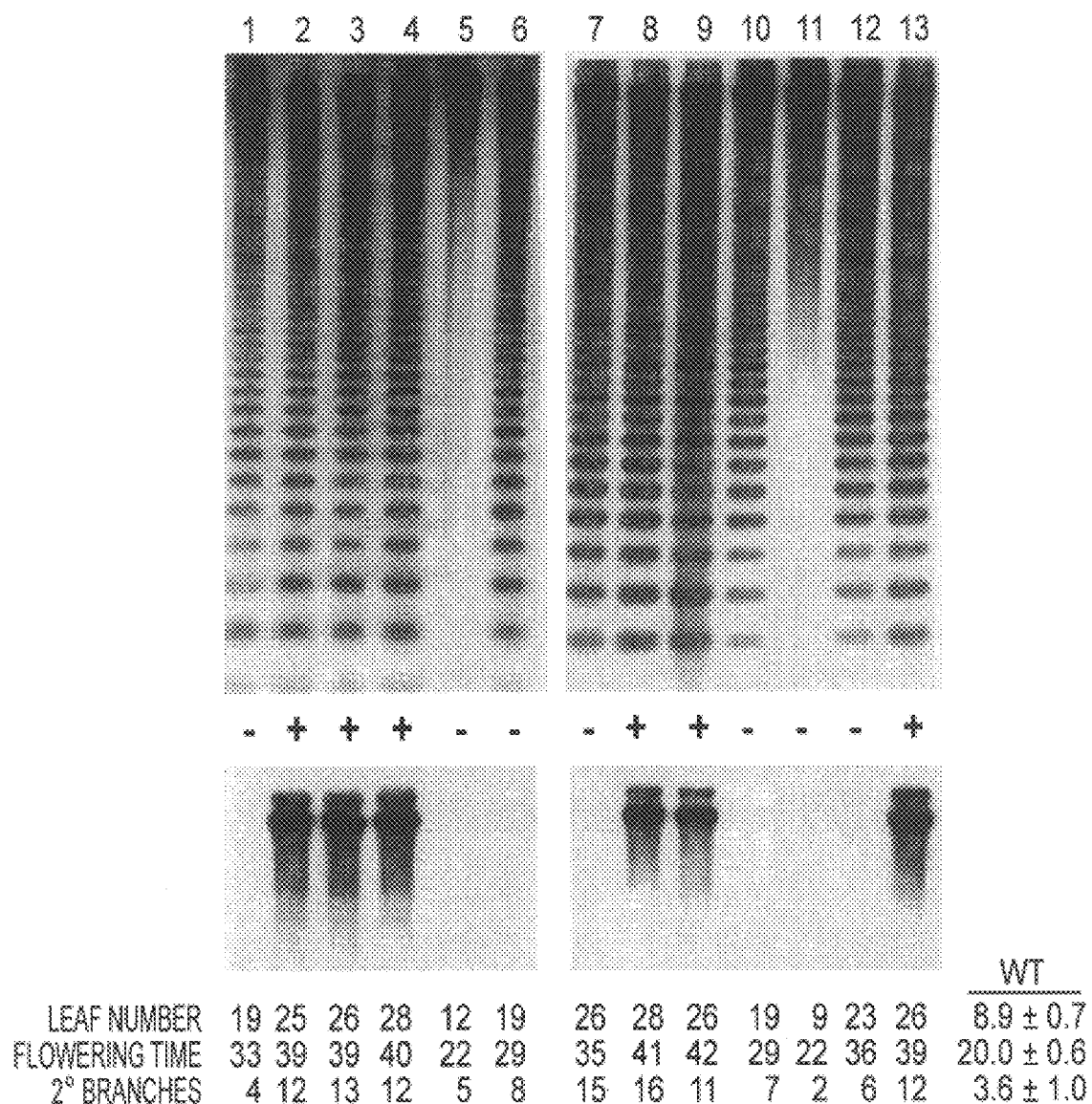
FIG. 3. Southern and phenotypic analyses of Tr246 outcross progeny. Genomic DNAs (4 μg/lane) from outcross progeny of strong antisense line Tr246 to wild-type Arabidopsis (Columbia strain with no mutations) were digested with Hpa II (FIG. 3 upper panels) or Eco RI (FIG. 3 lower panels). Southern analyses were done as described above. Filters were probed with the 180-bp centromere repeat (Martinez-Zapater et al. (1985) (FIG. 3 upper panels) or the CaMV 35S promoter fragment from pMON530 (FIG. 3 lower panels). Symbols indicate the presence (+) or absence (−) of the antisense transgene. Phenotypic data for each individual plant are shown below each lane. Plants were grown under continuous light at 21° C.

Genomic DNAs (4 μg/lane) from outcross progeny of strong antisense line Tr246 to wild-type Arabidopsis (Columbia strain with no mutations) were digested with Hpa II (FIG. 3 upper panels) or Eco RI (FIG. 3 lower panels). Southern analyses were done as described above. Filters were probed with the 180-bp centromere repeat (J. M. Martinez-Zapater, et al., (1985)) (FIG. 3 upper panels) or the CaMV 35S promoter fragment from pMON530 (FIG. 3 lower panels). Symbols indicate the presence (+) or absence (−) of the antisense transgene. Phenotypic data for each individual plant are shown below each lane. Plants were grown under continuous light at 21° C.

4. Control of DNA Methylation Through Antisense Expression

To address the role of DNA methylation in plant development, an antisense strategy was used to interfere with MET1 a DNA methyltransferase (MTase) gene of Arabidopsis, previously cloned by homology to the mouse gene (FIG. 1) (E. J. Finnegan, et al., (1993)). The MET1 (cDNA B5-2) used in these experiments was cloned independently; it lacked 436 base pairs (bp) downstream of the deduced transaction start site and differed from the published sequence by a thymine-to-cytosine substitution at position +2,981. The MET1 gene represents one member of a small gene family in Arabidopsis (E. J. Finnegan, et al., (1993)) that maps to position 68.9 on chromosome 5, nonallelic to the ddm1 locus (The MET1 gene was mapped with an Eco RI polymorphism between Arabidopsis ecotypes WS and W100 with RI lines (Dupont) and is nonallelic to ddm1 locus. T. Kakutani, et al., (1995)). The MET1 gene is expressed in seedling, vegetative, and floral tissues; in the inflorescence, expression is seen at highest levels in meristematic cells by in situ RNA hybridization.

To inhibit expression of the MET1 gene, an antisense construct (FIG. 1), consisting of a 4.3-kb MET1 cDNA in the antisense orientation under the control of a constitutive viral promoter (CaMV 35S), was introduced, into Arabidopsis strain Columbia. In one experiment, a total of nine primary transformants (TO generation) were recovered; progeny tests indicated that six lines that were further characterized contained single-locus transferred DNA (T-DNA) insertions. All transformations and analyses used an Arabidopsis strain Columbia line homozygous for a mutation at the g/1 locus as a marker (but otherwise wild type), except as noted by Agrobacterium-mediated transformation (N. Bechtold, et al., *Acad. Sci. Paris* 315: 1,194 (1993)).

Six single-locus lines were identified by kanamycin segregation. Southern blot analyses revealed that all lines contained independent insertions consisting of tandem repeats of the T-DNA. The plants used in this study represent the kanamycin-resistant progeny of T1 outcrosses from single-locus lines Tr242, 243, 244, 245, and 248. Before germination, all seeds were plated on MS media (Gibco) with (all transgenic lines) or without (controls) kanamycin (50 μg/ml, Sigma) and incubated for 3 days at 4° C. in the dark. Growth conditions were 16 hours light, 8 hours dark at 21° C., except as noted. Seedlings were transplanted into soil 8 days after germination.

Methylation patterns in repetitive DNA sequences were examined by Southern (DNA) hybridization (J. Chen, et al., in *The Maize Handbook*, M. Freeling, et al., (Springer-Verlag, New York, 1994), pp. 525–527 S. L. Dellaporta, et al., ibid, pp. 559–572). Genomic DNAs were digested with the isochizomers Hpa II or Msp I (FIG. 2, upper panels) and probed with a centromeric repeat or a 5S ribosomal DNA (rDNA) sequence; both repeats are methylated in wild-type genomic DNA (A. Vongs, et al., (1993)). Hpa II digestion is inhibited if either cytosine in the CCGG target site is methylated; Msp I can cleave $C^{5m}CGC$ but not $^{5m}CCGG$ (M. Nelson, et al., *Nucleic Acids Res.* 19: 2,045 (1991)).

With both probes, Hpa II digestion revealed a high extent of demethylation in three of six antisense lines (Tr244, 246, and 248; designated "weak") showed near wild-type levels of methylation. Msp I digestion was more complete in strong antisense lines contain substantial demethylation of these repeated sequences at $C^{5m}CGG$ and $5^{m}CCGG$ sites.

Digestion of wild-type genomic DNA with Eco RII and Bst NI, isochizomers with differential sensitivity to cytosine methylation in the motif $C^{5m}C(A/T)GG$, showed only minor differences in wild-type DNA when probed with the centromere repeat and 5S rDNA probes suggesting C(A/T)G methylation may not be prevalent.

Figures 2A, 2B:
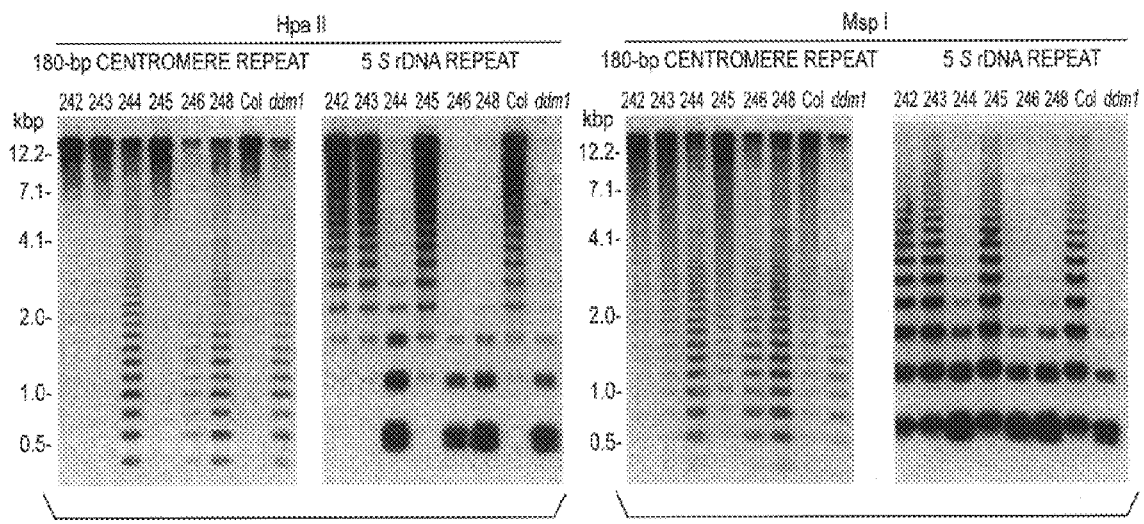
FIG. 2. Southern analysis of repetitive and single-copy DNA methylation patterns. Total genomic DNA (3 μg/lane) from antisense lines, wild-type, and the ddm1 mutant were digested with Hpa II (left panels) or Msp I (right panels), subjected to electrophoresis in 0.8% agarose, and transferred to Zeta-Probe membranes (Bio-Rad) and hybridized to probes as follows: (Upper panels) filters were probed with a 180-bp centromere repeat (J. M. Martinez-Zapater, et al., Mol. Gen. Genet, 204: 417 (1985)) and 5S rDNA (B. R. Campbell, et al., Gene 112: 225 (1992)); (Lower panels) filters were probed with four single-copy gene probes—PHOSPHORIBOSYLANTHRANILATE TRANSFERASE 1 (PAT1), PROLIFERA (PRL), CONSTITUTIVELY PHOTOMORPHOGENIC 1 (COP1), and ERECTA (ER). Digestion of wild-type genomic DNA with Eco RII and Bst N1, isochizomers with differential sensitivity to cytosine methylation in the motif $C^{5m}$C(A/T)GG, showed only minor differences in wild-type DNA when probed with the centromere repeat and 5S rDNA probes suggesting C(A/T)G methylation may not be prevalent-shown by differential Hpa II-Msp I digestion of wild-type DNA to contain $C^{5m}$CGG methylation M. J. Ronemus, et al., data not shown. The panel on the right was hybridized to a control gene, LEAFY (LFY) (D. Weigel, et al., Cell 59: 843 (1992)), shown not to be methylated in wild-type DNA.
Figures 2C, 2D, 2E, 2F, 2G:
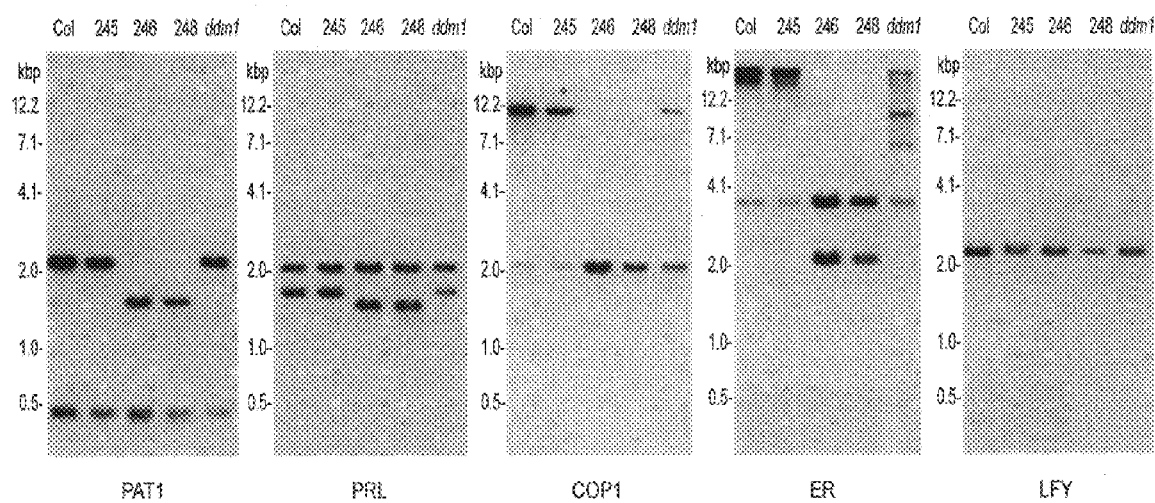

DNA methylation was examined at four single-copy gene sequences (A. B. Rose, et al., *Plant Physiol.* 100: 582 (1992); P. S. Springer, et al., *Science* 268: 877 (1995); X. W. Deng, et al., *Cell* 71: 191 (1992); K. U. Torii, et al, *Plant Cell* 8: 735 (1995)) (FIG. 2, lower panels). Substantial demethylation of all four genes was seen only in the strong antisense lines; the ddm1 mutant showed little or no demethylation relative to wild-type DNA, consistent with published reports (A. Vongs, et al., (1993)). Total genomic levels of $5^{m}C$ were also measured in these lines by high-performance liquid chromatography HPLC conditions were as described (C. W. Gehrke et al., *J. Chromatogr.* 301: 199 (1984), with the following exceptions: genomic DNAs were isolated from plants immediately after the onset of flowering, treated with 20 μg of ribonuclease A (Sigma) for 30 min. at 37° C., followed by passage through a Sepharose CL-5B (Pharmacia) spin column. Nucleosides were resolved on a Varian Vista 5500 Liquid Chromatograph with a Rainin Dynamax 5 μg Spherical Microsorb C18 column (100 Å pore size, 4.5 mm inner diameter by 15 cm length) with a 20 min. isocratic gradient of 2.5% methanol, 50 mM $KH_2PO_5$ (pH 4.0), followed by a 10 min. linear gradient to 8.0% methanol, 50 ml $KH_2PO_5$ (pH 4.0). (Table 1).

Cytosine methylation levels in wild-type (6.4% of total genomic cytosine) and the decrease in the ddm1 mutant (75%) agree with previously published estimates (A. Vongs, et al., (1993)). Total genomic $5^{m}C$ content in strong lines Tr246 and Tr248 was reduced 71% relative to wild-type levels; the weak line Tr245 showed a 34% reduction. The decrease in $5^{m}C$ levels in the strong lines by a factor of 3.5 is comparable to reductions seen in the ddm1 mutant and the MTase knockout mouse (R. Li, et al., *Cell* 59: 915 (1992)). Unlike the pattern of demethylation of the ddm1 mutant, however, MET1 antisense expression resulted in substantial demethylation of both repetitive DNA and single-copy gene sequences.

Cytosine methylation levels in Arabidopsis wild-type, ddm1 mutant, and three antisense lines was determined by reversed-phase HPLC using the method of Gehrke et al., (1984), with the following exceptions: genomic DNAs were isolated from plants immediately after the onset of flowering, treated with 20 μg of ribonuclease A (Sigma) for 30 min. at 37° C., followed by passage through a Sepharose CL-5B (Pharmacia) spin column. Nucleosides were resolved on a Varian Vista 5500 Liquid Chromatograph with a Rainin Dynamax 5 μm Spherical Microsorb C18 column (100 Å pore size, 4.5 mm inner diameter by 15 cm length) with a 20 min. isocratic gradient of 2.5% methanol, 50 mM $KH_2PO_5$ (pH 4.0), followed by a 10 min. linear gradient to 8.0% methanol, 50 ml $KH_2PO_5$ (pH 4.0). All values presented in Table 1 represent the averages of two to four individual replicates and were calculated by integration of peak areas with Dynamax HPLC Method Manager v1.2 (Rainin). Percentages of total $5^{m}C$ content $[5^{m}C/(5^{m}C+C)]$ are normalized for absorbance differences between cytosine and $5^{m}C$.

TABLE 1

| Line | Total $5^{m}C$ (%) | % WT levels | % Decrease |
| --- | --- | --- | --- |
| Wild type | 6.38 ± 0.69 | 100 | 0 |
| Tr245 | 4.24 ± 0.59 | 66.5 | 33.5 |
| Tr246 | 1.84 ± 0.27 | 28.9 | 71.1 |
| Tr248 | 1.83 ± 0.16 | 28.7 | 71.3 |
| ddm1 | 1.60 ± 0.04 | 25.0 | 75.0 |

Quantitative aspects of vegetative and inflorescence traits are given for wild-type Columbia strain and six antisense lines in Table 2. Flowering time is measured in days after germination. Flowering time refers to the number of days elapsed from seed germination until emergence of an inflorescence bolt 0.5 to 1.0 cm in height; leaf number refers to the number of vegetative leaves initiated before emergence of the primary inflorescence; and secondary branches refers to the number of branches initiated on the primary inflorescence axis. Values are calculated from a minimum of four individual plants from each line. Pool sizes for each line were as follows: wild-type; TR242; TR245, n=5; Tr243 and Tr244, n=4; Tr245, n=11; and Tr248, n=15.

TABLE 2

| Line | Flowering time | Leaf number | Secondary branches |
| --- | --- | --- | --- |
| Wild type | 26.2 ± 1.7 | 9.2 ± 1.3 | 4.3 ± 0.5 |
| Tr242 | 24.5 ± 2.1 | 10.0 ± 1.4 | 4.5 ± 1.1 |
| Tr243 | 27.8 ± 0.4 | 11.0 ± 0.7 | 4.3 ± 0.4 |
| Tr244 | 47.7 ± 4.0 | 34.0 ± 5.7 | 20.3 ± 4.9 |
| Tr245 | 27.7 ± 7.5 | 11.5 ± 1.5 | 4.3 ± 0.8 |
| Tr246 | 45.9 ± 3.6 | 32.5 ± 3.2 | 20.7 ± 1.4 |
| Tr248 | 46.3 ± 4.7 | 32.9 ± 2.7 | 20.5 ± 2.0 |

Normal patterns of development were perturbed in strong antisense lines. Under long day conditions, six single-locus lines were identified by kanamycin segregation. Southern blot analyses revealed that all lines contained independent insertions consisting of tandem repeats of the T-DNA. The plants used in this study represent the kanamycin-resistant progeny of T1 outcrosses from single-locus lines Tr242, 243, 244, 245, and 248. Before germination, all seeds were plated on MS media (Gibco) with (all transgenic lines) or without (controls) kanamycin (50 μg/ml, Sigma) and incubated for 3 days at 4° C. in the dark. Growth conditions were 16 hours light, 8 hours dark at 21° C., except as noted. Seedlings were transplanted into soil 8 days after germination; Tr244, Tr246 and Tr248 plants initiated 30 to 35 vegetative nodes with delayed abaxial trichome production and flowered after 45 to 48 days (Table 2); these phenotypes were fully penetrant in all T-DNA-containing progeny of the strong antisense lines.

After a transition from vegetative to reproductive development, wild-type plants initiated a primary inflorescence axis with two to five secondary inflorescence branches subtended by cauline leaves, followed by an abrupt transition to the production of solitary floral meristems (Table 2) (S. Shannon, et al., Plant Cell 5: 539 (1993)). In strong antisense lines, the primary inflorescence shoot produced an average of 20 secondary branches (Table 2) before the production of flowers. The basal-most branches in strong antisense lines often assumed characteristics of vegetative rosettes, including enhanced spiral phyllotaxy of 10 to 20 vegetative-like leaves and shortened internodes, followed by the emergence of an inflorescence bolt recapitulating the primary inflorescence. Unlike wild-type plants, occasional secondary branches were produced apically to flowers in the transition zone. Early initiating flowers from strong antisense lines were normal in appearance and male-fertile, but were often female-sterile. Apical flowers initiated on secondary and tertiary inflorescences showed gross abnormalities, including a threefold increase in stamen number and sterile, incompletely fused carpets lacking stigmas. Despite the severe disruptions in floral morphology seen in these late-initiating flowers, no obvious defects in pollen viability or paternal transgene transmission were observed on the basis of segregation ratios of transgenes in outcrosses Kanamycin resistance segregated in a 1:1 ratio in all outcrosses from strong antisense lines.

One trivial explanation for the MET1 antisense pleiotropy is that it represents an indirect effect on the transgene rather than a direct consequence of genomic demethylation; however, several lines of evidence support a direct role for DNA methylation in development. Data collected and analyzed in additional experiments revealed an identical pleiotropy in 12 independent transgenic lines. In analyses of outcross progeny from strong antisense lines, the severe phenotype co-segregated with the presence of the transgene, and a slightly attenuated pleiotropy was seen in progeny that had lost the transgene but retained a demethylated genome (FIG. 3). The latter finding is not unexpected, because the rate of genomic remethylation is slow (A. Vongs, et al., (1993)). Phenotypic revertants seen among outcross progeny had reestablished near wild-type levels of genomic methylation (FIG. 3, lanes 5 and 11). In sum, it appears that demethylation is sufficient to maintain developmental pleiotrophy in the absence of the transgene, whereas genomic remethylation is required to restore a wild-type phenotype.

The demethylation phenotype produced by antisense inhibition of Arabidopsis MTase differs markedly from the phenotype produced by the treatment of Arabidopsis seeds with the nonmethylatable cytosine analog 5-azacytidine (5-azaC), but bears some similarity to the ddm1 mutant phenotype. 5-AzaC produces early flowering in some late-flowering strains and mutants of Arabidopsis (J. E. Burn, et al., Proc. Nat'l Acad. Sci. U.S.A. 90: 287 (1993)), but this effect has not been correlated with a quantitative decrease in cytosine methylation. More recent evidence suggests that the primary effect of 5-azaC treatment is due to toxicity resulting from covalent trapping of DNA MTase (R. J ütterman, et al., Proc. Nat'l Acad. Sci. USA 91: 11,797 (1994)) or 5-azaC incorporation into RNA. The overall level of demethylation in the ddm1 mutant is equivalent to that seen in the strong MET1 antisense lines, yet the phenotype exhibited by the MET1 antisense lines is much more severe and pleiotropic. This discrepancy may be due to substantial demethylation observed at single-copy gene sequences in MET1 antisense lines not seen in the ddm1 mutant.

On the basis of these studies, DNA methylation is shown to be an essential component in the process of phase transitions and meristem determinacy. Methylation may serve as a primary signal to restrict meristem determinacy, or it may represent a secondary process required to maintain an epigenetic state once established. Phase transitions involve an interplay of both cell autonomous and diffusible signals (R. S. Poethig, Science 250: 923 (1990)). Evidence that methylation may represent an autonomous component in this process comes from the observation that phase transitions are often irregular in strong antisense plan—the location of branches apical to flowers in the inflorescence transition zone may represent an autonomous switching of individual cells in the meristem resulting in developmental mosaicism. Methylation effects have also been shown to be progressive in the plant meristem (R. Martienssen, et al., Genes Dev. 4: 331(1990)), and it is intriguing to speculate that a methylation gradient might be established during meristem growth to serve as an autonomous signal that directs meristem determinacy. In this light, the strong antisense phenotype could be explained by delayed establishment of this hypothetical gradient. Such a model predicts that meristem potential becomes progressively more epigenetically restrictive and that repression cascades will be an underlying theme in plant determinacy, a process implicit in the pathway controlling inflorescence and floral development in Arabidopsis (M. D. Wilkinson, et al., Plant Cell 7: 1,485 (1995)).

EXAMPLE 2

Plants with increased rates of development

To generate plants with increased amount of methylated DNA, Arabidopsis plants were altered to contain an expression unit that expresses cytosine methyl transferase under the control of the CaMV 35S promoter or another plant promoter. The cDNA encoding the MET1 protein from Arabidopsis described above was used to generate expression units in which the MET1 encoding sequence was placed under the regulatory control of the CaMV 355 promoter or the flower promoter AP3.

The expression units were introduced into a plant using Agrobacterium as described above. Transformed tissues were identified and plants were regenerated from the transformed tissue.

An analysis of the rate of development was performed and it was found that plants having an increased amount of methylated DNA produced flowers at 10 to 12 days following germination, compared to 26 days for non-altered plants.

EXAMPLE 3

General Methods for Decreasing the Rate of Development in a Plant

The Description of the Invention above provides a detailed outline for the various methods herein disclosed for altering the amount of DNA methylation present in a plant. The Examples provide the results of applications of the methods herein described. The following is intended to provide a non-limiting summary of the typical steps employed when altering a plant using the present methods.

1. Select Plant

The present methods can be applied to any plant that can be altered using molecular techniques. As discussed above, there are numerous commercially exploited plants whose value would be increased by either shortening the time required for maturation into seed producing plants or where it is desirable to increase biomass or seed yield. The first step in applying the present methods is to select as plant. Although it is preferable to select a plant that has had methods for expression, transformation and regeneration developed, most plants, though applied effort, can be transformed and regenerated using methods known in the art.

As part of choosing a plant, one needs to choose whether to increase or decrease the rate of maturation. As provided above, to increase the rate of maturation, the plant is altered so as to contain an increased amount of methylated DNA while to decrease the rate of maturation, the plant is altered so as to contained a decreased amount of methylated DNA.

2. Chose the alteration method/target that is to be employed

The second step may be to decide which method to employ to alter the plant. As provided above, the amount of DNA methylation can be decreased by inactivating or decreasing the activity of the methylase gene while the amount of DNA methylation can be increased by activating or increasing the methylase activity within the cell.

DNA methylation can be decreased by (1) the use of antisense expression units, (2) creating knockout mutations, (3) forcing the formation of triple helixes, and equivalent methods thereto.

DNA methylation can be increased by (1) the use of methylase expression units, (2) increasing the activity of endogenous methylases and equivalent methods thereto.

3. Apply the chosen method to the chosen plant

Once a plant and target/methods are chosen, the skilled artisan simply alters the plant using the chosen method, such as those outlined herein, and plants are selected based on the level of DNA methylation, the expression of the transgene, physiologic effects and equivalent methods thereto.

It should be understood that the foregoing discussion and examples merely present a detailed description of certain preferred embodiments. It therefore should be apparent to those of ordinary skill in the art that based on the above description of the invention and the specific Examples provided, a skilled artisan can readily adapt the present invention for use with any plant that can be altered by using molecular techniques. All articles and texts that are identified above are incorporated by reference in their entirety.

What is claimed is:

1. A method of slowing the rate of maturation of a plant wherein the method comprises inhibiting the expression of any and all methyltransferase genes in one or more plant cells of the plant by transforming the one or more plant cells with an antisense construct of methyltransferase cDNA.

2. A method of increasing the time required for a plant to mature wherein the method comprises:
   a). inhibiting expression of any and all methyltransferase genes of a plant cell according to the method of claim 1; and
   b). regenerating a plant from the plant cell of step a).

3. The method of claim 1 or 2 wherein the inhibition of any and all methyltransferase genes results in a reduction of DNA methylation by about 10% to about 25%.

4. The method of claim 1 or 2 wherein the inhibition of any and all methyltransferase genes results in a reduction of DNA methylation by about 25% to about 50%.

5. The method of claim 1 or 2 wherein the inhibition of any and all methyltransferase genes results in a reduction of DNA methylation by about 50% to about 75%.

6. A method of increasing the flowering time in days after germination of a plant wherein the method comprises inhibiting the expression of any and all methyltransferase genes in one or more plant cells of the plant by transforming the one or more plant cells with an antisense construct of methyltransferase cDNA.

7. The method of claim 6 wherein the inhibition of any and all methyltransferase genes results in a flowering time in days after germination which is from about 1.5 to about 2.5 times greater than the flowering time in days after germination of wild type plants.

8. A method of increasing the leaf number of a plant wherein the method comprises inhibiting the expression of any and all methyltransferase genes in one or more plant cells of the plant by transforming the one or more plant cells with an antisense construct of methyltransferase cDNA.

9. The method of claim 8 wherein the inhibition of any and all methyltransferase genes results in a leaf number which is from about 2.5 to about 3.5 times greater than the leaf number of wild type plants.

10. A method of increasing the number of secondary branches of a plant wherein the method comprises inhibiting the expression of any and all methyltransferase genes in one or more plant cells of the plant by transforming the one or more plant cells with an antisense construct of methyltransferase cDNA.

11. The method of claim 10 wherein the inhibition of any and all methyltransferase genes results in a number of secondary branches which is from about 4.5 to about 5.0 times greater than the secondary branch number of wild type plants.

12. A plant with a slower rate of maturation produced by inhibiting the expression of any and all methyltransferase genes in the plant by transforming of the plant with an antisense construct of methyltransferase cDNA, wherein the plant has a flowering time in days after germination which is from about 1.5 to about 2.5 times greater than the flowering time in days after germination of wild type plants.

13. A plant with an increased leaf number produced by inhibiting the expression of any and all methyltransferase genes in the plant by transforming the plant with an antisense construct of methyltransferase cDNA, wherein the plant has a leaf number which is from about 2.5 to about 3.5 times greater than the leaf number of wild type plants.

14. A plant with an increased number of secondary branches produced by inhibiting the expression of any and all methyltransferase genes in the plant by transforming the plant with an antisense construct of methyltransferase cDNA, wherein the plant has a number of secondary branches which is from about 4.5 to about 5.0 times greater than the secondary branch number of wild type plants.

15. A transforming vector comprising a transcription promoter operably linked to the nucleic acid sequence coding for MET1 Arabidopsis gene, wherein the nucleic acid sequence is operably linked to the transcription promoter in an antisense orientation.

16. The transforming vector of claim 15 wherein the transforming vector includes nucleic acid sequences coding for one or more additional methyltransferase genes.

17. A plant transformed with the transforming vector of claim 15 or claim 16.

18. A method of increasing the biomass of a plant wherein the method comprises inhibiting the expression of any and all methyltransferase genes in one or more plant cells of the plant by transforming the one or more plant cells with an antisense construct of methyltransferase cDNA.

19. A method of increasing the vegetative growth of a plant wherein the method comprises inhibiting the expression of any and all methyltransferase genes in one or more plant cells of the plant by transforming the one or more plant cells with an antisense construct of methyltransferase cDNA.

20. A plant with a greater biomass produced by inhibiting the expression of any and all methyltransferase genes in the plant by transforming the plant with an antisense construct of methyltransferase cDNA, wherein the plant has a biomass greater than the biomass of wild type plants.

21. A plant with greater vegetative growth produced by inhibiting the expression of any and all methyltransferase genes in the plant by transforming the plant with an antisense construct of methyltransferase cDNA, wherein the plant has a vegetative growth greater than the vegetative growth of wild type plants.

* * * * *